United States Patent
Chang et al.

(10) Patent No.: US 9,902,682 B2
(45) Date of Patent: Feb. 27, 2018

(54) 5-BROMO-2-(ALPHA-HYDROXYPENTYL) BENZOIC ACID SODIUM SALTS IN DIFFERENT CRYSTAL FORMS, AND PREPARATION METHOD THEREOF

(71) Applicant: Zhejiang Ausun Pharmaceutical Co., Ltd., Zhejiang (CN)

(72) Inventors: Junbiao Chang, Zhengzhou (CN); Chuanjun Song, Zhengzhou (CN)

(73) Assignee: Zhejiang Ausun Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/905,199

(22) PCT Filed: Jul. 10, 2014

(86) PCT No.: PCT/CN2014/081954
§ 371 (c)(1),
(2) Date: Jan. 14, 2016

(87) PCT Pub. No.: WO2015/007181
PCT Pub. Date: Jan. 22, 2015

(65) Prior Publication Data
US 2016/0168069 A1    Jun. 16, 2016

(30) Foreign Application Priority Data

Jul. 17, 2013 (CN) .......................... 2013 1 0299084
Jul. 3, 2014 (CN) .......................... 2014 1 0313214

(51) Int. Cl.
*C07C 63/70* (2006.01)
*C07C 51/09* (2006.01)
*C07C 51/60* (2006.01)

(52) U.S. Cl.
CPC .............. *C07C 63/70* (2013.01); *C07C 51/09* (2013.01); *C07C 51/60* (2013.01); *C07B 2200/13* (2013.01)

(58) Field of Classification Search
None
See application file for complete search history.

(56) References Cited

FOREIGN PATENT DOCUMENTS

| CN | 1594270 A | 3/2005 |
| CN | 1243541 C | 3/2006 |

(Continued)

OTHER PUBLICATIONS

English translation of International Search Report for PCT/CN2014/081954, 2 pages.
English translation of CN101402565B, 14 pages.

*Primary Examiner* — Clinton Brooks
*Assistant Examiner* — Jennifer C Sawyer
(74) *Attorney, Agent, or Firm* — Senniger Powers LLP

(57) ABSTRACT

The present invention discloses 5-bromo-2-(α-hydroxypentyl)benzoic acid sodium salt in different crystal forms and the preparation methods thereof, and belongs to the field of pharmaceutical chemistry. Said different crystal forms of 5-bromo-2-(α-hydroxypentyl)benzoic acid sodium salt include: amorphous 5-bromo-2-(α-hydroxypentyl)benzoic acid sodium salt, crystal form A of 5-bromo-2-(α-hydroxypentyl)benzoic acid sodium salt, and crystal form B of 5-bromo-2-(α-hydroxypentyl)benzoic acid sodium salt. The different crystal forms of 5-bromo-2-(α-hydroxypentyl)benzoic acid sodium salt obtained according to the present invention have better stability and water-solubility than the mixed forms of 5-bromo-2-(α-hydroxypentyl)benzoic acid sodium salt, thus is advantageous for pharmaceutical use. Moreover, the different crystal forms of 5-bromo-2-(α-hydroxypentyl)benzoic acid sodium salt possess much better (Continued)

therapeutic effect than 5-bromo-2-(α-hydroxypentyl)benzoic acid potassium salt.

8 Claims, 3 Drawing Sheets

(56) References Cited

FOREIGN PATENT DOCUMENTS

| | | | |
|---|---|---|---|
| CN | 101054346 | A | 10/2007 |
| CN | 101402565 | B | 4/2009 |
| CN | 100554259 | C | 10/2009 |

5-BROMO-2-(ALPHA-HYDROXYPENTYL) BENZOIC ACID SODIUM SALTS IN DIFFERENT CRYSTAL FORMS, AND PREPARATION METHOD THEREOF

REFERENCE TO RELATED APPLICATIONS

This application is the 371 National Stage Application based on International PCT Application No. PCT/CN2014/081954, filed Jul. 10, 2014 which claims priority to Chinese Patent Application No. 201410313214.4, filed Jul. 3, 2014 and Chinese Patent Application No. 201310299084.9, filed Jul. 17, 2013.

TECHNICAL FIELD

The present invention relates to 5-bromo-2-(α-hydroxypentyl)benzoic acid sodium salt (BZP) in different crystal forms and preparation methods thereof, and belongs to the field of pharmaceutical chemistry.

TECHNICAL BACKGROUND

Up to now, about half of drug molecules are present in the form of salts and are administrated in the form of salts. By forming salts, physical and chemical properties of drugs can be improved, such as solubility, dissolution rate, bioavailability, hygroscopicity, flowability, bulk density, stability, melting point, milling property, convenience for preparation and purification, or the like. If the same drug has different crystal forms, the bioavailability of different crystal forms will be different. Moreover, the stability, flowability and compressibility of different crystal forms will be different. Thus, such different physical and chemical properties will influence use of the drug to some extent.

6-halo-3-butyl-1(3H)-isobenzofuranone compound has certain therapeutic effect on ischemic cerebrovascular disease, and can promote recovery of impaired neural function in patients. 6-halo-3-butyl-1(3H)-isobenzofuranone is substantially insoluble in water, thus it is generally prepared as halo-2-(α-hydroxypentyl)benzoic acid, so as to improve the solubility. However, halo-2-(α-hydroxypentyl)benzoic acid is very unstable under room temperature and is easy to convert to 6-halo-3-butyl-1(3H)-isobenzofuranone, therefore this is disadvantageous for administration. It can be stored at low temperature (4° C.) for limited storage period.

Chinese patent No. 01109795.7 discloses salts of 2-(α-hydroxypentyl)benzoic acid and the preparation method and use thereof in the first time, which relates to salts of monovalent metal ions, divalent metal ions and organic bases. It specifically discloses the salts of potassium, sodium, calcium, magnesium, zinc, aniline, benzylamine, morpholine, and diethylamine. Its specification also discloses effect of the potassium salt on brain infarction area in rats with local brain ischemia, effect of the potassium salt on platelet aggregation in rats, and protective effect of the potassium salt on ischemia of isolated heart and arrhythmias following reperfusion in rats, thereby indicating the potassium salt produces beneficial effect in said experiments. Chinese patent No. 200410048268.9 and Chinese patent No. 200610073077.7 respectively disclose the preparations and activity tests of the corresponding chiral salts of 2-(α-hydroxypentyl)benzoic acid. Chinese patent No. 200710054215.1 discloses the synthesis and activity test of the halogenated compound 6-halo-3-butyl-1(3H)-isobenzofuranone in the first time, wherein the halogenated compound 6-halo-3-butyl-1(3H)-isobenzofuranone has obviously better activity than butylphthalide. Chinese patent No. 200810230890.X discloses the preparation method of halogenated 2-(α-hydroxypentyl)benzoic acid salts compounds and pharmaceutical use thereof in the first time, which relates to salts of monovalent metal ions, divalent metal ions and organic bases. It specifically discloses the salts of sodium, potassium, calcium, and benzylamine. Its specification also discloses the activity of the halogenated 2-(α-hydroxypentyl)benzoic acid potassium salt for prevention and treatment of heart and brain ischemic diseases, for improving heart and brain circulatory disorders and anti-thrombotic effect, and the like, wherein activity of the halogenated 2-(α-hydroxypentyl)benzoic acid potassium salt is better than butylphthalide, 6-halo-3-butyl-1(3H)-isobenzofuranone, and 2-(α-hydroxypentyl)benzoic acid salt. However, the above patents do not relate to research of crystal forms of 5-halo-2-(α-hydroxypentyl)benzoic acid salts. Therefore, it is of practical importance to study different crystal forms of 5-bromo-2-(α-hydroxypentyl)benzoic acid sodium salt and to improve pharmaceutical stability and water-solubility of said compound, thereby meeting the requirements for administration. In the meantime, the different crystal forms of 5-bromo-2-(α-hydroxypentyl)benzoic acid sodium salt produce obviously better therapeutic effect than 5-bromo-2-(α-hydroxypentyl)benzoic acid potassium salt (CN ZL200810230890.X). Said better therapeutic effect has not been reported by any literatures in the art until now.

DISCLOSURE OF THE INVENTION

In order to improve stability and water-solubility of 5-bromo-2-(α-hydroxypentyl)benzoic acid sodium salt, the present invention studied different crystal forms of 5-bromo-2-(α-hydroxypentyl)benzoic acid sodium salt, and provides different crystal forms of 5-bromo-2-(α-hydroxypentyl)benzoic acid sodium salt. Another object of the present invention is to provide the methods for preparing the crystal forms.

5-bromo-2-(α-hydroxypentyl)benzoic acid sodium salt according to the present invention has the following structural formula, which has enantiomers:

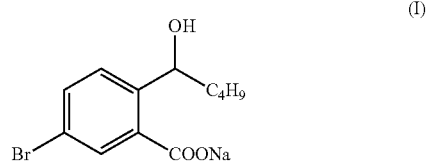

Said different crystal forms of 5-bromo-2-(α-hydroxypentyl)benzoic acid sodium salt include: amorphous 5-bromo-2-(α-hydroxypentyl)benzoic acid sodium salt, crystal form A of 5-bromo-2-(α-hydroxypentyl)benzoic acid sodium salt, and crystal form B of 5-bromo-2-(α-hydroxypentyl)benzoic acid sodium salt.

The XRPD pattern of amorphous 5-bromo-2-(α-hydroxypentyl)benzoic acid sodium salt generally has no obvious diffraction peak.

The present invention describes crystal form A of 5-bromo-2-(α-hydroxypentyl)benzoic acid sodium salt, characterized in having XRPD pattern with the diffraction peaks at 2θ values of 5.60, 16.46, 16.78, 18.77, 21.45, 32.28, 33.30, 33.49, 34.12, 36.14, 36.61, 37.87, 40.24, 41.32, 43.76, 44.92, 45.18, 47.23, 55.12, 56.73, 57.12, 62.78, wherein the error range of 2θ value is ±0.2.

The present invention describes crystal form B of 5-bromo-2-(α-hydroxypentyl)benzoic acid sodium salt, characterized in having XRPD pattern with the diffraction peaks at 2θ values of 5.72, 6.69, 9.93, 11.09, 11.84, 14.55, 16.42, 17.27, 17.80, 18.28, 19.86, 20.98, 22.21, 23.43, 23.88, wherein the error range of 2θ value is ±0.2.

A method for preparing amorphous 5-bromo-2-(α-hydroxypentyl)benzoic acid sodium salt: 6-bromo-3-butyl-1(3H)-isobenzofuranone and sodium hydroxideare are weighed and placed in a crystallizer, to which tetrahydrofuran and water are added, then the mixture is dissolved and reacted under a water bath at 60° C.; after completion of the reaction, the reaction mixture is distilled under reduced pressure to remove all the solvents to yield amorphous 5-bromo-2-(α-hydroxypentyl)benzoic acid sodium salt.

A method for preparing crystal form A of 5-bromo-2-(α-hydroxypentyl)benzoic acid sodium salt: amorphous 5-bromo-2-(α-hydroxypentyl)benzoic acid is weighed, to which a solution of NaOH in methanol is added, dissolved under ultrasound, and then the solvent is volatilized slowly; after solids are precipitated, the solids are dried under vacuum.

Method I for preparing crystal form B of 5-bromo-2-(α-hydroxypentyl)benzoic acid sodium salt: amorphous 5-bromo-2-(α-hydroxypentyl)benzoic acid is weighed, to which tetrahydrofuran is added, and then the solution is stirred at room temperature; an aqueous solution of sodium hydroxide is slowly added dropwise to the above-mentioned solution; after evaporation of solvents, solids are obtained, and dried under vacuum.

Method II for preparing crystal form B of 5-bromo-2-(α-hydroxypentyl)benzoic acid sodium salt: 6-bromo-3-butyl-1(3H)-isobenzofuranone and sodium hydroxide are weighed and placed in a flask; methanol is added to the flask, the resulting mixture is heated under reflux to react, and then methanol is evaporated off; ethyl acetate is added, the resulting mixture is shaken and the undissolved solids are filtrated off; ethyl acetate is evaporated off to yield solid compound, to which anhydrous diethyl ether is added to dissolve, and the resulting solution is maintained standing overnight and is filtrated.

The inventiveness of the present invention is based on that 5-bromo-2-(α-hydroxypentyl)benzoic acid sodium salt is prepared as crystals. Since different crystal forms of the same compound are significantly different in appearance, solubility, melting point, dissolution rate, bioavailability and the like, pharmaceutical stability, bioavailability and therapeutic effect will be affected. The crystal forms of 5-bromo-2-(α-hydroxypentyl)benzoic acid salt obtained according to the present invention have better stability and water-solubility than amorphous 5-halo-2-(α-hydroxypentyl)benzoic acid, thus are advantageous for pharmaceutical use.

EXAMPLES

Figure 1:
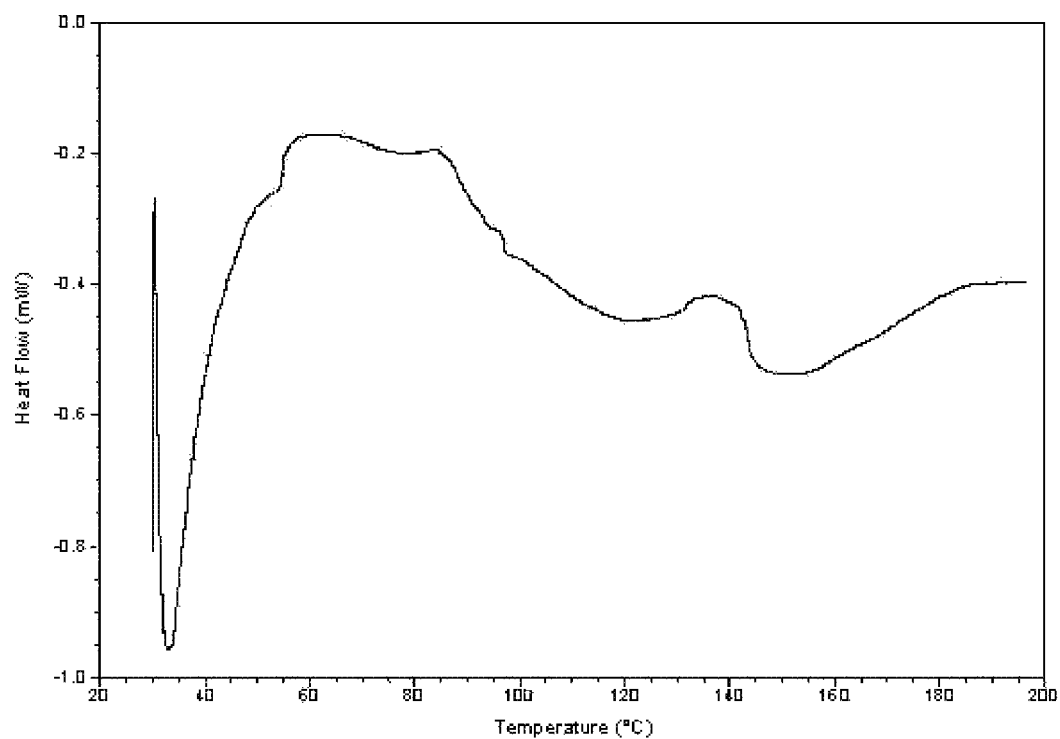
FIG. 1 is DSC pattern of amorphous 5-bromo-2-(α-hydroxypentyl)benzoic acid sodium salt.
Figure 2:
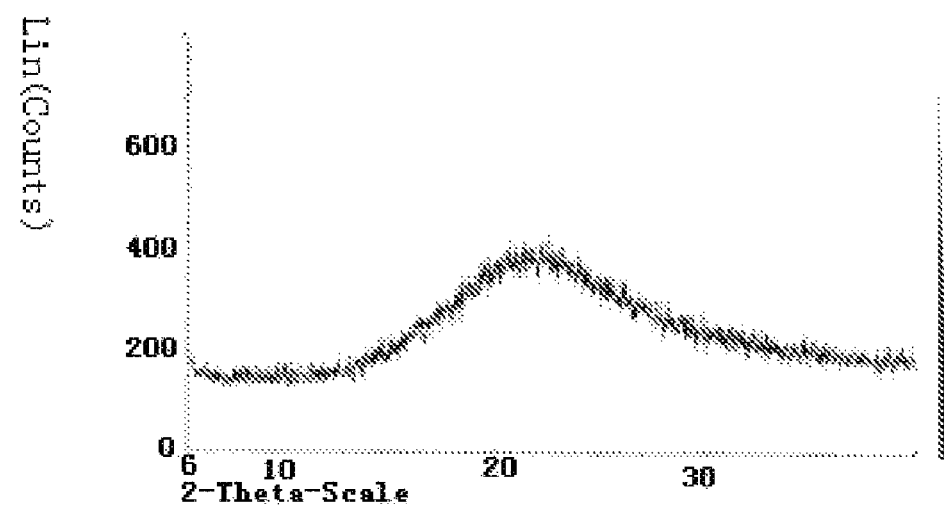
FIG. 2 is XRPD pattern of amorphous 5-bromo-2-(α-hydroxypentyl)benzoic acid sodium salt.
Figure 3:
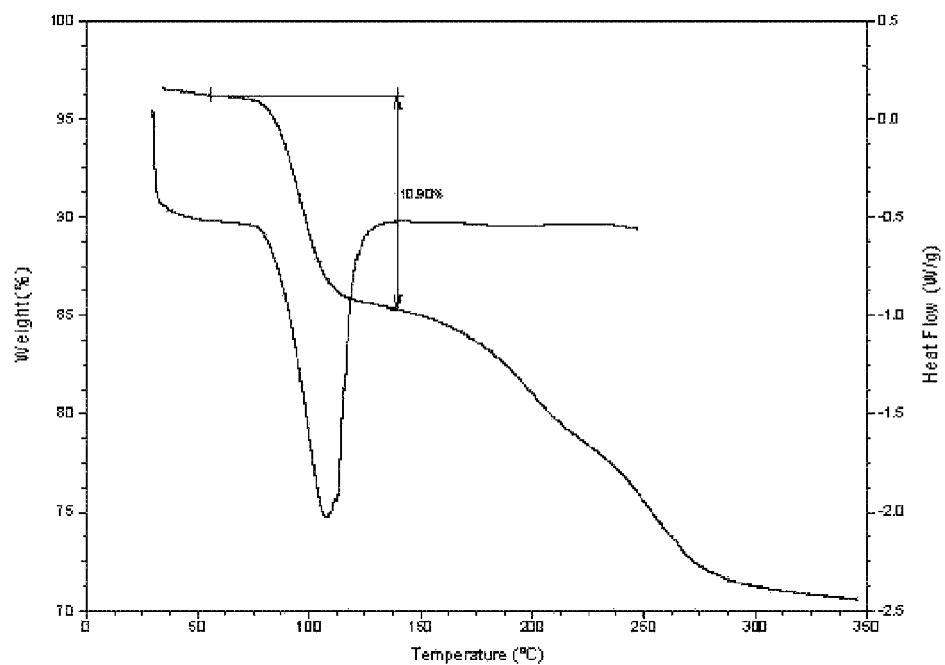
FIG. 3 is DSC/TGA pattern of crystal form A of 5-bromo-2-(α-hydroxypentyl)benzoic acid sodium salt.
Figure 4:
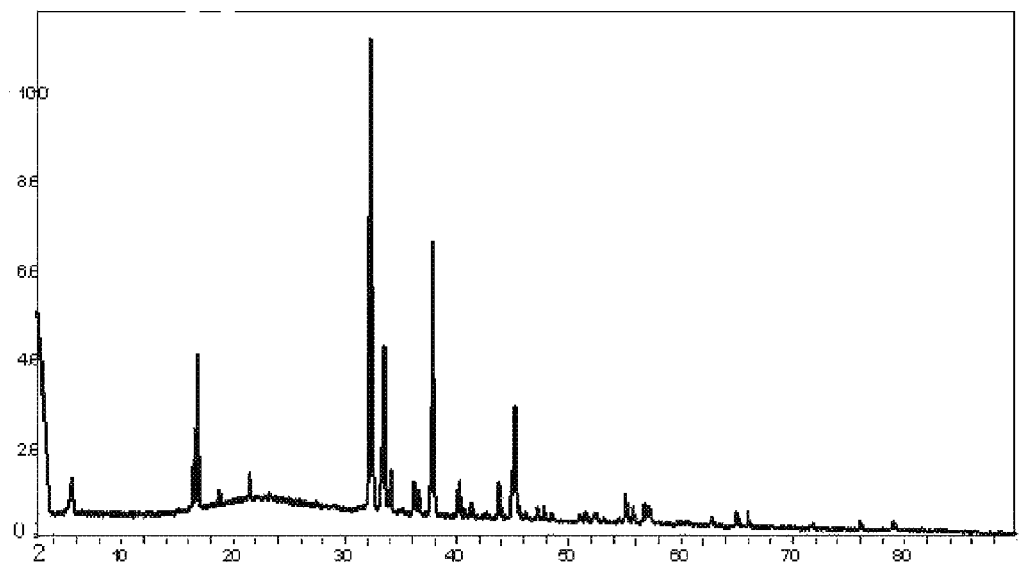
FIG. 4 is XRPD pattern of crystal form A of 5-bromo-2-(α-hydroxypentyl)benzoic acid sodium salt.
Figure 5:
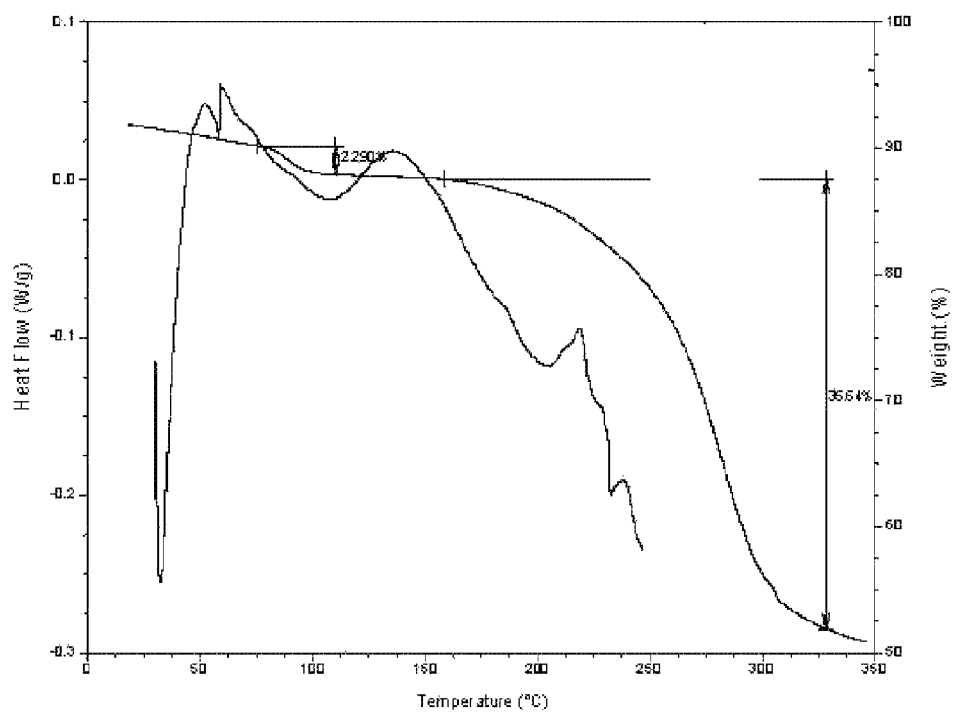
FIG. 5 is DSC/TGA pattern of crystal form B of 5-bromo-2-(α-hydroxypentyl)benzoic acid sodium salt.
Figure 6:
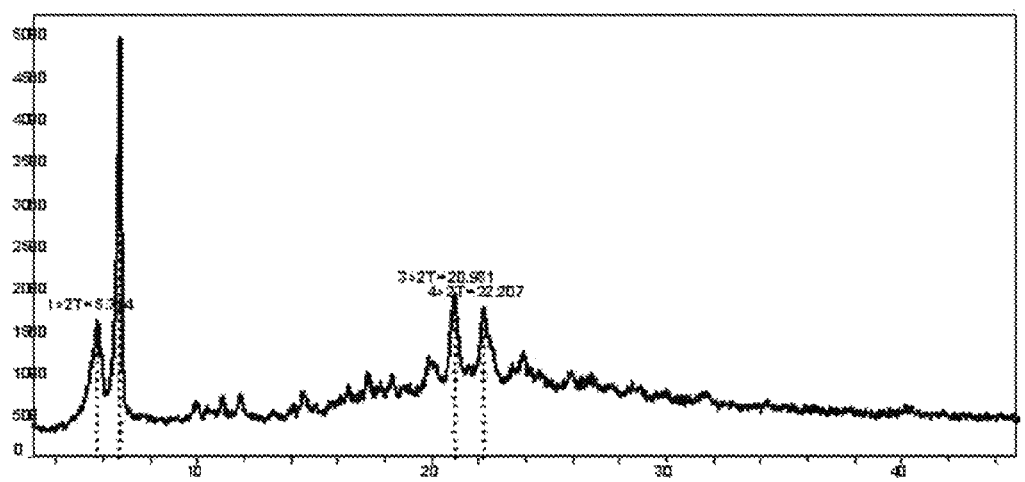
FIG. 6 is XRPD pattern of crystal form B of 5-bromo-2-(α-hydroxypentyl)benzoic acid sodium salt.

The following examples are used to help a skilled person in the art understand the present invention more deeply, but are not intended to limit the present invention in any ways.

Example 1: Preparation of Amorphous 5-Bromo-2-(α-Hydroxypentyl)Benzoic Acid Sodium Salt 3.5 g of 6-bromo-3-butyl-1(3H)-isobenzofuranone and 520 mg of sodium hydroxide were weighed and placed in a crystallizer, to which 40 ml tetrahydrofuran and 8 ml water were added, then the mixture was dissolved and reacted under a water bath at 60° C. After 3 hours, the reaction mixture was distilled under reduced pressure at 60° C. to remove all the solvents, to yield amorphous 5-bromo-2-(α-hydroxypentyl)benzoic acid sodium salt.

Example 2: Preparation of Crystal Form a of 5-Bromo-2-(α-Hydroxypentyl)Benzoic Acid Sodium Salt 350 mg of amorphous 5-bromo-2-(α-hydroxypentyl)benzoic acid was weighed, to which 2 ml solution of NaOH in methanol was added, dissolved under ultrasound, and then the solvent was volatilized slowly for 14 days. Solids were precipitated. The solids were dried under vacuum to yield crystal form A of 5-bromo-2-(α-hydroxypentyl)benzoic acid sodium salt.

Example 3: Preparation of Crystal Form B of 5-Bromo-2-(α-Hydroxypentyl)Benzoic Acid Sodium Salt (Method I)

1.15 g of amorphous 5-bromo-2-(α-hydroxypentyl)benzoic acid was weighed and placed in a 20-ml sample bottle with magnetically stirring at room temperature, to which 1 ml tetrahydrofuran was added. 120 mg of sodium hydroxide was weighed and dissolved in 8 ml water, and then the NaOH solution was slowly added into the above-mentioned solution dropwise. The resulting solution was subjected to rotary evaporation at 50° C. Solids were obtained, and dried under vacuum at room temperature to yield crystal form B of 5-bromo-2-(α-hydroxypentyl)benzoic acid sodium salt.

Example 4: Preparation of Crystal Form B of 5-Bromo-2-(α-Hydroxypentyl)Benzoic Acid Sodium Salt (Method II)

20 g of 6-bromo-3-butyl-1(3H)-isobenzofuranone and 4.46 g of sodium hydroxide were weighed and placed in a 500-ml round bottom flask. 300 ml methanol was added to the flask, and the resulting mixture was heated under reflux to react. Then methanol was evaporated off. 200 ml ethyl acetate was added. After the resulting mixture was shook adequately, the undissolved solids were filtrated off. Ethyl acetate was evaporated off to yield viscous white solid compound, and 300 ml anhydrous diethyl ether was added to dissolve. The resulting solution was maintained standing overnight and a large amount of white solid precipitated. The mixture was filtrated to yield crystal form B of 5-bromo-2-(α-hydroxypentyl)benzoic acid sodium salt.

Example 5: Effect of 5-Bromo-2-(α-Hydroxypentyl)Benzoic Acid Sodium Salt on Brain Infarction Volume and Brain Edema Volume in Rats with Local Brain Ischemia (1) Experimental Materials and Methods Wistar rats (50% of rats is female and another 50% of rats is male); 5-bromo-2-(α-hydroxypentyl)benzoic acid sodium salt (BZP, in the form of amorphous form, crystal form A and crystal form B, prepared according to the present invention), prepared in double distilled water; TTC is in the form of white powder, manufactured by Beijing Chemical Works.

Administration method: 5-bromo-2-(α-hydroxypentyl)benzoic acid sodium salt (BZP) was intravenously injected at one hour before MCAO, with the dosage of 12 mg/kg; 5-bromo-2-(α-hydroxypentyl)benzoic acid sodium salt (BZP) was used to intragastric administration at one hour before MCAO, with the dosage of 20 mg/kg. 2-(α-hydroxypentyl)benzoic acid potassium salt (NBP-K) was used as positive control, and its dosage (calculated in moles) is the same as that of 5-bromo-2-(α-hydroxypentyl)benzoic acid sodium salt, that is, the dosage of intravenous injection is 9.6 mg/kg, and the dosage of intragastric administration is 15.9 mg/kg.

Preparation of MCAO model: Establish a focal brain ischemia-reperfusion injury model by cerebral artery obstruction in rats with suture-occluded method. Rats were intraperitoneally injected with 10% chloral hydrate to anesthetize. Rats were fixed on back and the skin of neck center was incised. The left common carotid artery, external carotid artery, and internal carotid artery were subjected to blunt dissection. The pterygopalatine artery was ligated, only remaining cranial trunk of internal carotid artery; a prepared nylon rope (burning diameter 0.3 mm) was inserted via external carotid artery incision into the bifurcation of the jugular vein, and was pushed along the cranial direction of the internal carotid artery. Using the place of the bifurcation as starting point, after the rope was pushed forward about 17 mm, hand can feel force of resistance, indicating that the head section of nylon rope has been through the beginning of the middle cerebral artery. This indicates one side of the middle cerebral artery occlusion model was completed. Sutured the incision, remained the end of nylon line out of the skin. For reperfusion, the nylon line was gently pulled out. If feel force of resistance, this indicates the end of nylon line has returned to the trunk of external carotid artery, thereby accomplishing reperfusion.

Determination of infarction volume: After being subjected to ischemia for 2 hours and reperfusion for 24 hours, the heads of rats were cut off. Forebrain was removed and cut into six pieces, each piece being 2 mm. The pieces were stained with TTC, and incubated at 37° C. for 30 minutes. Normal issues were stained to be red, but the infarcted issues were stained to be white. Took photos with digital camera, and calculated the percentage of the infarcted area relative to the spherical area of brain by Photoshop.

(2) Results

Experimental results of model group: brain infarction volume was 53.42±4.65%, and brain edema volume was 13.66±3.46%.

The effect of intravenous injection and intragastric administration of 5-bromo-2-(α-hydroxypentyl)benzoic acid sodium salt (BZP) on brain infarction volume in rat MCAO model and the effect of intravenous injection and intragastric administration of 5-bromo-2-(α-hydroxypentyl)benzoic acid sodium salt (BZP) on brain edema volume in rat MCAO model were as follows:

Effect of intravenous injection of 5-bromo-2-(α-hydroxypentyl)benzoic acid sodium salt (BZP) on brain infarction volume in rat MCAO model

| Drug | Dosage (mg/kg) | n | Infarction volume (%) | Inhibition of infarction volume (%) |
|---|---|---|---|---|
| Pseudo-surgery group | | | 0 | 0 |
| Model group | | 10 | 53.42 ± 4.65 | |
| BZP (amorphous form) | 12 | 10 | 3.46 ± 2.94 aa | 93.52 |
| BZP (crystal form A) | 12 | 10 | 4.54 ± 1.73 aa | 91.50 |
| BZP (crystal form B) | 12 | 10 | 4.76 ± 1.45 aa | 91.09 |
| NBP-K | 9.6 | 10 | 24.35 ± 4.32$^{aa}$ | 54.42 | aa: $P < 0.01$, as compared with the model group;
**: $P < 0.01$, as compared with the NBP-K group.

Effect of intravenous injection of 5-bromo-2-(α-hydroxypentyl)benzoic acid sodium salt (BZP) on brain edema in rat MCAO model

| Drug | Dosage (mg/kg) | n | Edema (%) | Inhibition of edema (%) |
|---|---|---|---|---|
| Pseudo-surgery group | | | 0 | 0 |
| Model group | | 10 | 13.66 ± 3.46 | |
| BZP (amorphous form) | 12 | 10 | 2.56 ± 1.63 aa | 88.58 |
| BZP (crystal form A) | 12 | 10 | 3.24 ± 4.11$^{aa*}$ | 81.28 |
| BZP (crystal form B) | 12 | 10 | 4.20 ± 2.03a | 78.71 |
| NBP-K | 12 | 10 | 12.38 ± 1.29 | 9.37 | aa: $P < 0.01$, as compared with the model group;
*$P < 0.05$, as compared with the NBP-K group;
**: $P < 0.01$, as compared with the NBP-K group.

Effect of intragastric administration of 5-bromo-2-(α-hydroxypentyl)benzoic acid sodium salt (BZP) on brain infarction volume in rat MCAO model

| Drug | Dosage (mg/kg) | n | Infarction volume (%) | Inhibition of infarction volume (%) |
|---|---|---|---|---|
| Pseudo-surgery group | | | 0 | 0 |
| Model group | | 10 | 53.42 ± 4.65 | 0 |
| BZP (amorphous form) | 20 | 10 | 5.59 ± 2.35 aa | 89.05 |
| BZP (crystal form A) | 20 | 10 | 7.13 ± 2.98 aa | 86.65 |
| BZP (crystal form B) | 20 | 10 | 7.13 ± 2.98$^{aa**}$ | 86.03 |
| NBP-K | 15.9 | 10 | 22.28 ± 2.65$^{aa}$ | 58.3 | aa: $P < 0.01$, as compared with the model group;
**$P < 0.01$, as compared with the NBP-K group.

Effect of intragastric administration of 5-bromo-2-(α-hydroxypentyl)benzoic acid sodium salt (BZP) on brain edema in rat MCAO model

| Drug | Dosage (mg/kg) | n | Edema (%) | Inhibition of edema (%) |
|---|---|---|---|---|
| Pseudo-surgery group | | | 0 | 0 |
| Model group | | 10 | 13.66 ± 3.46 | |
| BZP (amorphous form) | 20 | 10 | 2.24 ± 1.66$^{aa}$** | 88.36 |
| BZP (crystal form A) | 20 | 10 | 2.7 ± 1.30$^{aa}$** | 87.55 |
| BZP (crystal form B) | 20 | 10 | 2.87 ± 1.56$^{aa}$** | 85.09 |
| NBP-K | 15.9 | 10 | 11.04 ± 1.48$^{aa}$** | 42.65 |

$^{aa}$P < 0.01, as compared with the model group;
*: P < 0.05, as compared with the NBP-K group;
**P < 0.01, as compared with the NBP-K group.

(3) Conclusion:

5-bromo-2-(α-hydroxypentyl)benzoic acid sodium salt can obviously reduce brain tissue injury induced by obstruction of cerebral arteries, reduce brain infarction volume and reduce brain edema volume in rats. At the same dosage, the activity of 5-bromo-2-(α-hydroxypentyl)benzoic acid sodium salt is obviously better than 2-(α-hydroxypentyl)benzoic acid potassium salt, and the activity of 5-bromo-2-(α-hydroxypentyl)benzoic acid sodium salt is also better than butylphthalide and halogenated 2-benzo[c]furanone known in the art.

Example 6: Results of Primary Toxicity Study of 5-Bromo-2-(α-Hydroxypentyl)Benzoic Acid Sodium Salt Data of acute toxicity and sub-acute toxicity of 5-bromo-2-(α-hydroxypentyl)benzoic acid sodium salt BZP (in amorphous form)

| | | BZP | | NBP-K | |
|---|---|---|---|---|---|
| Items | | ig | iv | ig | iv |
| LD50 (mg/Kg) | Mouse | 927 | 323 | 880 | 303 |
| | Rat | 726 | 246 | 623 | 230 |
| Sub-acute (mg/Kg) | Rat | >20 | >12 | >20 | >12 |

Note:
ig 20 mg/kg;
iv 12 mg/kg.

Example 7: Sub-Acute Toxic Effect of 5-Bromo-2-(α-Hydroxypentyl)Benzoic Acid Sodium Salt (in Amorphous Form) on Liver and Kidney Functions in Rats

| | | Groups | | |
|---|---|---|---|---|
| Items | Sex | Control group | ig (20 mg/kg) | iv (12 mg/kg) |
| ALT | F | 43.38 ± 6.69 | 35.10 ± 8.61 | 38.00 ± 9.82 |
| AST | F | 219.40 ± 55.38 | 168.00 ± 17.19* | 202.40 ± 68.12 |
| | M | 5.30 ± 0.87 | 4.92 ± 0.75 | 5.34 ± 1.33 |
| AST/ALT | F | 246.20 ± 129.61 | 135.29 ± 48.13* | 184.80 ± 68.59 |
| | M | 4.35 ± 0.05 | 2.74 ± 1.62* | 3.96 ± 1.20 |
| Total Proteins (TP) | F | 48.52 ± 2.46 | 46.63 ± 1.07 | 49.00 ± 0.79 |
| | M | 41.70 ± 2.04 | 40.26 ± 15.78 | 53.40 ± 8.69* |
| Albumin (ALB) | F | 33.52 ± 1.98 | 32.43 ± 1.14 | 33.96 ± 1.71 |
| | M | 27.74 ± 1.38 | 28.98 ± 7.34 | 36.90 ± 6.72* |
| Total Bilirubin (TBIL) | F | 2.58 ± 0.63 | 2.10 ± 0.40 | 2.72 ± 0.67 |
| | M | 5.20 ± 3.88 | 2.24 ± 1.50** | 3.10 ± 1.23* |
| Blood urea nitrogen (BUN) | F | 3.69 ± 0.46 | 3.80 ± 0.59 | 4.00 ± 0.43 |
| | M | 4.54 ± 0.72 | 2.76 ± 1.09** | 3.46 ± 0.72* |
| Creatinine (CRE) | F | 59.80 ± 5.02 | 57.50 ± 3.11 | 55.40 ± 2.30 |
| | M | 60.00 ± 7.25 | 38.80 ± 25.62* | 66.60 ± 15.09 |
| Creatinine kinase (CK) | F | 924.20 ± 445.66 | 776.00 ± 437.68 | 636.80 ± 536.05 |
| | M | 634.50 ± 37.48 | 938.60 ± 553.43* | 762.00 ± 351.72 |

Note:
*P < 0.05,
**P < 0.01, as compared with the same gender of control group.

Example 8: Sub-Acute Toxic Effect of 5-Bromo-2-(α-Hydroxypentyl)Benzoic Acid Sodium Salt (in Amorphous Form) on Blood Routine Tests

| | | Groups | | |
|---|---|---|---|---|
| Items | Sex | Control group | ig (20 mg/kg) | iv (12 mg/kg) |
| RBC | F | 6.97 ± 1.80 | 4.51 ± 3.30 | 6.95 ± 1.06 |
| | M | 7.67 ± 0.53 | 7.61 ± 0.28 | 7.86 ± 0.40 |
| HGB | F | 126.60 ± 30.22 | 117.00 ± 19.70 | 125.60 ± 16.68 |
| | M | 140.33 ± 5.69 | 134.00 ± 19.13 | 141.40 ± 7.20 |
| PLT | F | 1129.75 ± 109.48 | 1146.00 ± 74.22 | 1075.00 ± 41.70 |
| | M | 1118.67 ± 53.26 | 1258.20 ± 281.33 | 1087.20 ± 56.34 |
| WBC | F | 5.50 ± 2.49 | 4.44 ± 2.24 | 5.20 ± 1.53 |
| | M | 4.67 ± 2.22 | 5.18 ± 0.71 | 5.66 ± 2.23 |

-continued

| Items | Sex | Control group | ig (20 mg/kg) | iv (12 mg/kg) |
|---|---|---|---|---|
| Neutrophil (NEU) | F | 22.20 ± 7.96 | 28.44 ± 10.20 | 21.44 ± 2.74 |
|  | M | 17.23 ± 5.66 | 23.88 ± 5.48 | 22.16 ± 4.14 |
| Lymphocyte | F | 71.26 ± 7.86 | 66.45 ± 11.13 | 73.62 ± 2.16 |
| (LYM) | M | 73.53 ± 9.11 | 70.84 ± 3.99 | 72.50 ± 4.66 |
| Monocyte (MON) | F | 4.56 ± 2.12 | 2.05 ± 1.74** | 3.62 ± 0.63 |
|  | M | 7.20 ± 323 | 4.93 ± 1.91* | 3.80 ± 0.70* |
| Eosinophil (EOS) | F | 0.70 ± 0.50 | 0.23 ± 0.12** | 0.76 ± 0.50 |
|  | M | 0.63 ± 0.45 | 0.56 ± 0.50 | 0.60 ± 0.29 |
| Basophil | F | 1.28 ± 0.85 | 1.43 ± 1.17 | 0.56 ± 0.15** |
| (BAS) | M | 1.40 ± 0.20 | 0.62 ± 0.25* | 0.40 ± 0.12** |

Note:
*$P < 0.05$,
**$P < 0.01$, as compared with the same gender of control group.

Example 9: Sub-Acute Toxic Effect of 5-Bromo-2-(α-Hydroxypentyl)Benzoic Acid Sodium Salt (in Amorphous Form) on Blood Coagulation Functions in Rats

| Items | Sex | Control group | ig (20 mg/kg) | iv (12 mg/kg) |
|---|---|---|---|---|
| APTT | F | 25.6 ± 2.3 | 22.8 ± 5.9 | 22.3 ± 8.5 |
| (sec) | M | 25.5 ± 3.2 | 26.5 ± 3.2 | 23.7 ± 2.1 |
| PT | F | 18.0 ± 2.1 | 17.5 ± 2.2 | 18.8 ± 3.3 |
| (sec) | M | 18.4 ± 1.8 | 16.4 ± 3.4 | 17.5 ± 2.0 |
| FIB | F | 7.31 ± 0.51 | 7.22 ± 0.97 | 6.63 ± 0.95 |
| (g/l) | M | 6.66 ± 1.08 | 7.03 ± 0.29 | 6.28 ± 0.55 |
| TT | F | 26.3 ± 2.5 | 27.3 ± 2.4 | 27.5 ± 2.8 |
| (sec) | M | 28.5 ± 1.7 | 26.9 ± 5.9 | 27.1 ± 3.8 |

Example 10: Effect of 5-Bromo-2-(α-Hydroxypentyl)Benzoic Acid Sodium Salt (in Amorphous Form) on Body Weight of Rats

| Groups | Sex | Day 1 BW | Day 6 BW | Day 6 ΔW (%) | Day 11 BW | Day 11 ΔW (%) | Day 16 BW | Day 16 ΔW (%) | Day 21 BW | Day 21 ΔW (%) | Day 24 BW | Day 24 ΔW (%) |
|---|---|---|---|---|---|---|---|---|---|---|---|---|
| Control | M | 178 ± 6 | 207 ± 8 | 16 ± 5 | 253 ± 4 | 22 ± 3 | 295 ± 10 | 66 ± 6 | 330 ± 20 | 85 ± 9 | 341 ± 24 | 92 ± 10 |
|  | F | 172 ± 6 | 188 ± 6 | 9 ± 2 | 216 ± 10 | 15 ± 3 | 260 ± 6 | 37 ± 5 | 258 ± 11 | 50 ± 6 | 259 ± 10 | 52 ± 7 |
| ig group | M | 183 ± 8 | 210 ± 8 | 15 ± 3 | 245 ± 12 | 17 ± 5 | 280 ± 18 | 53 ± 14 | 320 ± 18 | 75 ± 14 | 337 ± 18 | 84 ± 14 |
|  | F | 179 ± 12 | 192 ± 16 | 7 ± 4 | 205 ± 14 | 7 ± 2* | 224 ± 11 | 25 ± 4* | 230 ± 15 | 29 ± 6** | 235 ± 12 | 31 ± 5** |
| iv group | M | 179 ± 13 | 204 ± 7 | 14 ± 6 | 236 ± 6 | 14 ± 2* | 270 ± 6 | 51 ± 10 | 296 ± 8 | 66 ± 15* | 304 ± 10 | 71 ± 16* |
|  | F | 182 ± 13 | 195 ± 12 | 7 ± 2 | 200 ± 15 | 3 ± 2** | 212 ± 14 | 21 ± 7** | 223 ± 20 | 23 ± 6** | 221 ± 19 | 21 ± 6** |

Note:
ΔW (%) means the percentage of increase of body weight of rats at Day X as compared with the body weight at Day 1.
*$P < 0.05$, as compared with the percentage of increase of body weight of the same gender in control group,
**$P < 0.01$, as compared with the percentage of increase of body weight of the same gender in control group.
Note:
ig: 20 mg/kg;
iv: 12 mg/kg.

Example 11

Comparison of stability and solubility of amorphous 5-bromo-2-(α-hydroxypentyl)benzoic acid sodium salt (BZP, in the form of amorphous form), crystal form A of 5-bromo-2-(α-hydroxypentyl)benzoic acid sodium salt (BZP crystal form A) and crystal form B of 5-bromo-2-(α-hydroxypentyl)benzoic acid sodium salt (BZP crystal form B) with 5-bromo-2-(α-hydroxypentyl)benzoic acid sodium salt (a mixture, CN ZL200810230890.X) in water and methanol solution

| Drug | Solubility in water (g/mL) | Stability (hours) | Solubility in methanol (g/mL) | Stability (hours) |
|---|---|---|---|---|
| BZP (amorphous) | 2.98 | >24 | 1.89 | >24 |
| BZP (Form A) | 2.36 | >20 | 1.80 | >24 |
| BZP (Form B) | 2.43 | >24 | 1.63 | >24 |
| BZP (mixture) | 2.13 | >12 | 1.58 | >12 |

The invention claimed is:

1. Amorphous 5-bromo-2-(α-hydroxypentyl)benzoic acid sodium salt, prepared by a method comprising:

placing 6-bromo-3-butyl-1(3H)-isobenzofuranone and sodium hydroxide in a crystallizer to form a mixture, adding tetrahydrofuran and water solvents to the mixture; and reacting the mixture containing the solvents under a water bath at 60° C. to form a reaction mixture;

wherein after the reaction is complete, the reaction mixture is distilled under reduced pressure to remove the tetrahydrofuran and water solvents therefrom and to yield amorphous 5-bromo-2-(α-hydroxypentyl)benzoic acid sodium salt.

2. A method for preparing amorphous 5-bromo-2-(α-hydroxypentyl)benzoic acid sodium salt according to claim 1, the method comprising:

placing 6-bromo-3-butyl-1(3H)-isobenzofuranone and sodium hydroxide in a crystallizer to form a mixture, adding tetrahydrofuran and water solvents to the mixture; and reacting the mixture containing the solvents under a water bath at 60° C. to form a reaction mixture;

wherein after the reaction is complete, the reaction mixture is distilled under reduced pressure to remove the tetrahydrofuran and water solvents therefrom and to yield amorphous 5-bromo-2-(α-hydroxypentyl)benzoic acid sodium salt.

3. A method of reducing brain tissue injury induced by obstruction of cerebral arteries comprising administering the amorphous 5-bromo-2-(α-hydroxypentyl)benzoic acid sodium salt of claim 1.

4. A method of reducing brain infarction volume comprising administering the amorphous 5-bromo-2-(α-hydroxypentyl)benzoic acid sodium salt of claim 1.

5. A method of reducing brain edema volume comprising administering the amorphous 5-bromo-2-(α-hydroxypentyl)benzoic acid sodium salt of claim 1.

6. The method of claim 3 wherein administration of the amorphous 5-bromo-2-(α-hydroxypentyl)benzoic acid sodium salt of claim 1 comprises intravenous administration or intragastric administration.

7. The method of claim 4 wherein administration of the amorphous 5-bromo-2-(α-hydroxypentyl)benzoic acid sodium salt of claim 1 comprises intravenous administration or intragastric administration.

8. The method of claim 5 wherein administration of the amorphous 5-bromo-2-(α-hydroxypentyl)benzoic acid sodium salt of claim 1 comprises intravenous administration or intragastric administration.

* * * * *